United States Patent [19]

Peters, Jr. et al.

[11] Patent Number: 5,013,669

[45] Date of Patent: May 7, 1991

[54] MASS PRODUCIBLE BIOLOGICALLY ACTIVE SOLID PHASE DEVICES

[75] Inventors: Donald F. Peters, Jr., Campbell; Lawrence C. Dumont, Santa Cruz, both of Calif.

[73] Assignee: SmithKline Diagnostics, Inc., San Jose, Calif.

[21] Appl. No.: 202,100

[22] Filed: Jun. 1, 1988

[51] Int. Cl.$^5$ .............................................. G01N 33/543
[52] U.S. Cl. .................................. 436/518; 435/7.100; 435/7.720; 435/803; 435/805; 436/528; 436/529; 436/530; 436/531; 436/535; 436/807; 436/824
[58] Field of Search ................ 422/56, 61, 57, 68, 422/70; 435/7, 176, 177, 178, 179, 180, 803, 805, 7.1, 7.92–7.95; 436/524, 527, 529, 530, 531, 535, 807, 824; 427/341; 101/DIG. 3, DIG. 30; 210/635

[56] References Cited

U.S. PATENT DOCUMENTS

| | | |
|---|---|---|
| 3,793,445 | 2/1974 | Updike et al. |
| 3,951,748 | 4/1976 | Devlin .............................. 436/528 X |
| 3,966,897 | 6/1976 | Renn et al. |
| 4,003,792 | 1/1977 | Mill et al. ............................... 195/63 |
| 4,334,027 | 6/1982 | Klein et al. ........................... 435/178 |
| 4,446,232 | 5/1984 | Liotta ...................................... 435/7 |
| 4,452,892 | 6/1984 | Rosevear ............................. 435/176 |
| 4,469,796 | 9/1984 | Axen et al. ...................... 436/535 X |
| 4,530,900 | 7/1985 | Marshall ................................ 435/7 |
| 4,609,707 | 9/1986 | Nowinski et al. .............. 436/535 X |
| 4,743,545 | 5/1988 | Torobin .......................... 435/176 X |
| 4,780,409 | 10/1988 | Monji et al. .................... 436/539 X |
| 4,912,032 | 3/1990 | Hoffman ................................ 435/7 |

OTHER PUBLICATIONS

D. L. Marshall, "A New Immunoassay Separation Technique Using Reversibly Soluble Polymers," *Analytical Letters 15,* 1947–1465 (1982).

W. A. Colburn, "Radioimmunoassay for Fluoxymesterone (Halotestin (R))," *Steroids 25,* 43–52 (1975).

*Primary Examiner*—Robert J. Warden
*Assistant Examiner*—Carol A. Spiegel
*Attorney, Agent, or Firm*—William H. May; Gary T. Hampson; Michael B. Farber

[57] ABSTRACT

A solid phase binding member for the detection of an analyte in a test sample is described. The binding member comprises: (1) a solid support having micropores; (2) a polymer reversibly water-soluble before its application to the solid support; and (3) a ligand covalently attached to the polymer, the ligand interacting specifically with the analyte. The solid support can have micropores throughout or on its surface, and can be rayon, paper, fabric, plastic, agarose or polyacrylamide beads, glass, microcrystalline cellulose, or acid-treated plastic. The polymer can be carrageenan or sodium alginate. The ligand can be an antibody, a univalent antigen-binding fragment of an antibody, an antigen, a hapten, an enzyme, a hormone, or a single-stranded nucleic acid. Methods of use of the binding member are also described involving incorporation into a test device. The test device can be a dip stick, a hollow vessel, a slide, or a porous bead. A process for producing the binding member is also described, comprising solubilizing the water-soluble polymer, impregnating the solid support with the conjugate, and cross-linking the polymer to fix the conjugate to the support. Also described are methods for detecting an analyte specifically binding the ligand of a solid phase binding member. The basic method comprises: (1) exposing the solid phase binding member to an analyte-containing solution; (2) removing the binding member from the solution and washing it; and (3) determining the presence of analyte bound to the binding member, preferably quantitatively.

53 Claims, No Drawings

MASS PRODUCIBLE BIOLOGICALLY ACTIVE SOLID PHASE DEVICES

BACKGROUND

This invention relates to solid phase devices useful for detecting biologically active analytes.

For many purposes, including the production of solid phase devices, it is essential to anchor ligands such as biologically active molecules to a solid support. The anchoring of such molecules to a solid support is necessary for the production of solid phase materials. These binding members are often incorporated into solid phase devices in the form of test strips. Such test strips are currently in wide use. They are frequently used by clinicians for initial screening of patients for a variety of conditions or diseases. Examples include test strips for the detection of glucose and ketone bodies in the urine in screening for diabetes, strips for the detection of occult blood in the stool in screening for early indications of cancer of the colon, and strips to detect the presence of the hormone human chorionic gonadotropin in urine as a pregnancy test. Such test strips are also now widely used by patients themselves at home for monitoring chronic conditions such as urinary sugar in diabetes. With increasing societal concern over drug abuse, an additional application of such assays has been screening urine samples for drugs of abuse such as heroin, cocaine, marijuana, or amphetamines in large-scale drugtesting programs. Such test strips must be inexpensive to make, simple to use even by untrained personnel, and reproducible in their results, avoiding false positives and false negatives.

The biologically active molecules anchored to the support can be, for example, enzymes, hormones, antibodies, or antigens. A number of supports are used for such test strips, including plastic and paper.

Other test devices can also require anchoring ligands to solid supports as part of their construction. These test devices can be hollow vessels such as test tubes or centrifuge tubes, slides for the performance of immunoassays such as single immunodiffusion, radial immunodiffusion, and rocket immunoelectrophoresis, or porous beads for affinity chromatography.

There are several methods that have been previously used to couple biologically active molecules to a solid support. Two of the prior methods used are: (i) direct covalent attachment of the biologically active molecule to the support; and (ii) passive adsorption, particularly to plastics. Although both of these methods have been widely used, they have important disadvantages, particularly for the preparation of test strips.

Direct covalent attachment of the biologically active molecule to the solid support can require difficult, time-consuming, and expensive steps to activate the solid support with a cross-linking reagent. A commonly used method, for example, involves pretreatment of the support with the cross-linking reagent glutaraldehyde. One version of this procedure, as described in P. Tijssen, "Practice and Theory of Enzyme Immunoassays," Amsterdam, Elsevier, 1985, p. 306, requires a four-hour incubation of the solid support with glutaraldehyde, several washing steps, a three-hour incubation of the solid support with the molecule to be coupled, several more washing steps, a further one-hour incubation with an amino acid to block the remaining activated sites on the solid support, and still more washing steps. The cross-linking reaction with glutaraldehyde can be difficult to control, and can result in inactivation of the biologically active molecule.

Other coupling agents than glutaraldehyde can be used for covalent attachment. Examples of these agents include carbodiimides, cyanogen bromide, and carbonyldiimidazole. These coupling agents have many of the same disadvantages as glutaraldehyde, except that the reactions can perhaps be better controlled with these reagents.

Another serious disadvantage in the use of the direct covalent attachment method is that it is often difficult to activate some widely-used solid supports, such as glass and some plastics.

The method of passive adsorption of proteins to plastics is easier to perform than covalent binding. However, it also has disadvantages. The process works at best poorly with solid supports other than plastic. In most cases, molecules other than proteins and some lipid and lipopolysaccharide antigens cannot be effectively adsorbed. Some very important classes of biologically active molecules, such as native DNA, small oligopeptides, and haptens, are at best poorly adsorbed to the plastic. A relatively long period of incubation is frequently needed, and the reagents usually must be refrigerated during this long period of incubation. Further, the adsorption of proteins onto plastic can be difficult to control. Much desorption of the bound protein can occur during subsequent incubation. The efficiency of the binding can vary unpredictably with different proteins and with different brands of plastic. Moreover, for uncertain reasons, there can be considerable variability in the binding of protein from one well on a single plate to another well. Nonspecific interactions between proteins added later during the assay process and plastic can also occur. These nonspecific interactions can diminish the reproducibility of assays carried out in such plates, and may have to be suppressed in some cases by the addition of extraneous protein, such as non-immune goat serum. These problems make the passive adsorption process unsuitable for preparation of test strips.

Other methods for attaching biologically active molecules to a solid support have been sought. Several prior workers have employed, for various purposes, covalently attaching a biologically active molecule of interest to a monomer or sol, the monomer or sol subsequently being incorporated in some manner into a polymer or gel.

Mill et al., in U.S. Pat. No. 4,003,792, issued Jan. 28, 1977, disclose chemical conjugates of acid polysaccharides and biologically active complex organic molecules, particularly conjugates capable of forming soluble sodium salts and insoluble calcium salts. Formation of the conjugate is generally effected through basic amino or phenolic hydroxyl groups of the biologically active molecule to the acid groups of the polysaccharide.

Klein et al., in U.S. Pat. No. 4,334,027, issued June 8, 1982, disclose preparation of gel beads containing an immobilized enzymatically active substance.

Marshall, in U.S. Pat. No. 4,530,900, issued July 23, 1985, and in "A New Immunoassay Separation Technique Using Reversibly Soluble Polymers," *Analytical Letters* 15, 1457–1465 (1982), describes the use of reversibly soluble polymers in an immunoassay. In this procedure, antibody is coupled to sodium alginate with water-soluble carbodiimide resulting in a conjugate.

The conjugate can be removed from solution as desired by converting the polymer to an insoluble form by pH adjustment or addition of metal ions. Two general immunoassay procedures are also described using these conjugates.

Other methods of immobilizing biological molecules have also been described. Liotta, in U.S. Pat. No 4,446,232, issued May 1, 1984, describes an enzyme immunoassay using a two-zoned device incorporating bound antigens. This device operates by competition for the enzyme-linked antibodies between free antigen in the test sample and immobilized antigen bound to the device.

Another procedure for immobilization of biological materials was disclosed by Rosevear, in U.S. Pat. No. 4,452,892, issued June 5, 1984. Rosevear describes a process forming a hydrogel, the hydrogel comprising a biologically active material, a polymerizable material, and a viscosity enhancing agent. The polymerizable material can chemically polymerize, be cross-linked by calcium, or gel on cooling.

These prior methods can have problems in the mass production of dip sticks, such as failure to couple the ligand covalently to the polymer, failure to bind the polymer rapidly to a solid support, and difficulty in retaining the activity of the attached ligand when resolubilizing the polymer. Accordingly, none of these disclosures teaches a mass producible dip stick for biologically active analytes or a method for producing such dip sticks.

Therefore there is a need for binding members such as dip sticks that can be produced rapidly and inexpensively. These dip sticks must preserve the biological activity of the attached molecules, be usable with a wide variety of biologically active molecules and solid supports, and be sufficiently stable to be stored in the dry state.

SUMMARY

A solid phase binding member for an analyte in a test sample according to the present invention satisfies this need. The binding member which I prepared comprises:

(1) a solid support having micropores;

(2) a polymer reversibly water-soluble before its application to the solid support, the polymer being in its solid phase and impregnating at least a portion of the micropores of the solid support; and (3) a ligand covalently attached to the polymer, the ligand being capable of interacting specifically, directly or indirectly, with the analyte.

In the binding member, the solid support can have micropores throughout, or can have micropores only on the surface. Exemplary solid supports having micropores throughout include rayon, paper, fabric, plastic, agarose beads, polyacrylamide beads, glass, silica gel and microcrystalline cellulose. Exemplary solid supports having micropores on the surface include acid-treated plastic such as polycarbonate, etched metals, and fritted glass.

Typically, the surface concentration of polymer impregnating the portion of the micropores of the solid support is sufficiently low that analyte can pass freely through the support in the absence of ligand. This surface concentration is typically no greater than about 0.01 g of polymer per square centimeter of area of the solid support, and can be as low as about 0.002 g of polymer per square centimeter of area of the solid support.

The polymer of the present invention is reversibly water-soluble before its application to the solid support. Preferably the transition of the polymer from the solid phase to the solution phase can occur readily at a temperature of about 25° C. or less. Optionally, the polymer can be reversibly water-soluble after its application to the solid support. This allows the resolubilization of the polymer and recovery of bound analyte if desired. The polymer can be sodium alginate or carrageenan.

In the binding member, the ligand is typically biologically active. A "biologically active" molecule is an organic molecule that occurs in vivo and is part of a physiological system or any organic molecule that is functionally related to such a molecule. When the ligand Is biologically active, optimally the transition of the polymer from the solution phase to the solid phase is readily reversible under conditions preserving the biological activity of the ligand. The ligand can be an antibody, a univalent antigen-binding fragment of an antibody, an antigen, a hapten, an enzyme, a hormone, a receptor for a hormone, or a single-stranded or double-stranded nucleic acid.

A wide variety of test devices can incorporate the binding member. For example, the test device can be a dip stick, or a hollow vessel, in which case the binding member is incorporated on the inner liquid-contacting surface of the vessel. The test device can also be a slide, in which case the binding member is incorporated on the surface. It can also be a porous bead, as for use in affinity chromatography.

The binding member can be produced by a process comprising the steps of:

(1) covalently coupling the ligand to the polymer in solution, the polymer being capable of reversible transition between a solid phase and a solution phase before being fixed to a solid support, the covalent coupling of the ligand to the polymer producing a ligand-polymer conjugate;

(2) impregnating at least a portion of the solid support having micropores with the ligand-polymer conjugate; and (3) cross-linking the water-soluble polymer such that the ligand-polymer conjugate is fixed to the solid support.

If the polymer is not already in solution, a preliminary step can comprise solubilizing the polymer.

Coupling of the ligand to the polymer in solution can occur by means of several coupling agents. For example, the coupling can occur by the reaction of amino groups on the ligand and carboxyl groups on the polymer with 1-ethyl-3-3dimethylaminopropyl) carbodiimide. Alternatively, the coupling can occur by reaction of carboxyl groups on the ligand and hydroxyl groups on the polymer with carbonyldiimidazole, or by reaction of amino groups on the ligand and hydroxyl groups on the polymer with cyanogen bromide.

The cross-linking of the water-soluble polymer can occur by introducing $Ca^{2+}$ ions to the solid support. The concentration of polymer in solution prior to cross-linking is preferably from about 0.2% to about 1% by weight, and more preferably from about 0.2% to about 0.5% by weight. This concentration is typically greater than about 0.2% by weight. Typically, the step of impregnating the solid support with the conjugate comprises applying the conjugate to the solid support on a printing press. This can be performed with a doctor blade and roller. The step of cross-linking the water-soluble polymer can occur simultaneously with impregnation of the solid support with the conjugate, or can occur after impregnation. When cross-linking occurs after impregnation, the polymer can be allowed to dry after impregnation and before cross-linking. In this case, the solid support with the dried but uncross-linked polymer can be stored in that condition for a period of time.

Optimally, cross-linking of the water-soluble polymer is completed within about one second after it is initiated.

More specifically, this general method can be applied to a rapid process for producing a test strip on a printing press. This process comprises the steps of:

(1) covalently coupling the ligand to the polymer in solution, the covalent coupling of the ligand to the polymer producing a ligand-polymer conjugate;

(2) placing the ligand-polymer conjugate into a suspension suitable for printing onto a solid support using the printing press;

(3) impregnating at least a portion of a solid support having micropores with the ligand-polymer conjugate by printing the suspension containing the conjugate onto the solid support using the high-speed printing press; and (4) cross-linking the water-soluble polymer such that the liquid-polymer conjugate is fixed to the solid support to form the test strip. Optimally, the step of cross-linking the water-soluble polymer occurs on the printing press simultaneously with the impregnation of the solid support with the conjugate, and is completed within about one second after it is initiated.

The binding member is used for detecting an analyte specifically binding, directly or indirectly, to the ligand of the binding member. Several detection methods make use of unique properties of the binding member of the present invention.

In one of these methods, the water-soluble polymer is resolubilized so that bound analyte can be recovered free of the ligand and solid support for its determination. This method comprises the steps of:

(1) binding the analyte to the solid phase binding member, the binding occurring in the test sample into which the binding member is placed;

(2) removing the binding member from the test sample and washing the binding member, thereby separating analyte bound to the binding member from unbound analyte; and (3) then determining the presence of analyte originally bound to the binding member after resolubilizing the water-soluble polymer so that bound analyte can be recovered free of the ligand and solid support for determination.

In another of these methods, the analyte bound to the ligand of the binding member is detected through the production of a detectable product itself bound to the binding member. The detectable product is produced by the action of a signal producing system This method comprises the steps of:

(1) binding the analyte to the solid phase binding member, the binding occurring in the test sample into which the binding member is placed;

(2) removing the binding member from the test sample and washing the binding member, thereby separating analyte bound to the binding member from unbound analyte; and (3) then determining the presence of analyte bound to the binding member by reacting the washed binding member with a signal producing system that produces a detectable product when analyte is bound to the binding member, the detectable product also being bound to the binding member.

These and other features, aspects, and advantages of the present invention will become better understood from the accompanying description and appended claims.

DESCRIPTION

This invention relates to solid phase binding members for an analyte in a test sample. The binding members are produced by anchoring a ligand to a solid support. The invention includes the binding members themselves, methods for preparing them, apparatus incorporating the binding members into a test device, and methods for detecting an analyte specifically binding, directly or indirectly, the ligand of a binding member, particularly in enzymatic and immunological assays.

The preparation of these binding members makes use of certain water-soluble polymers such as sodium alginate or carrageenan, to which an appropriate ligand is covalently attached. The ligand is typically a biologically active molecule, but can be any other molecule that can be covalently attached to the reversibly soluble polymer. The soluble form of this polymer-ligand conjugate can then adhere to the surface or penetrate the fibers or pores of a solid support. The polymer is then cross-linked in the solid support, thereby anchoring the ligand to the solid support.

1. The Binding Member

The binding member of the present invention comprises a solid support, a polymer reversibly water-soluble before its application to the solid support, and a ligand covalently attached to the polymer. The solid support typically has micropores, either throughout or only on its surface, and a portion of those micropores is impregnated by the polymer in the formation of the binding member. The portion of the micropores impregnated can range from under 10% to nearly 100% of the micropores, but is typically approximately 25%. In the formation of the binding member, the polymer must be able to solidify or insolubilize rapidly under conditions not adversely affecting the ability of the ligand to bind to the analyte or the specificity of the desired ligand-analyte interactions.

The surface concentration of the polymer in the support is preferably sufficiently low that analyte can pass through the support in the absence of ligand. This surface concentration can range from as much as about 0.1 gram of polymer per square centimeter of solid support down to as little as about 0.001 gram per square centimeter, but is typically about 0.01 gram per square centimeter.

a. The Solid Support

The solid support can either have micropores throughout or only on its surface. In either case, the number of these micropores per square unit of area must be large enough to allow a sufficient quantity of the polymer to penetrate and bind to the support. This number depends on the porosity of the solid support and on whether the micropores extend through the solid support or are restricted to the surface of the solid support. What is a sufficient quantity of the polymer depends on the nature of the analyte and the test to be performed, but when the analyte binds directly to the ligand, there preferably is a large enough quantity of polymer bound to the solid support such that all analyte normally found in the test sample can be bound to the ligand in the ligand-polymer conjugate. The surface concentration of polymer required to provide this quantity of polymer, expressed in terms of mass of polymer per unit area of solid support, varies with the total surface area of the solid support exposed to test sample. This quantity is typically about 0.01 gram of polymer per square centimeter of solid support.

Examples of suitable solid supports having micropores throughout include microcrystalline cellulose layers such as those commonly used for thin-layer chromatography, filter paper, fabrics such as nylon or rayon, silica gel, and beads of agarose or polyacrylamide.

Examples of suitable solid supports with micropores on the surface include plastics such as polycarbonates treated with acid to etch the surface, etched metals, and fritted glass.

Whether the solid support has micropores throughout or only on the surface, the analyte must be able to pass through the pores of the support so that the analyte can contact the polymer-ligand conjugate for binding to the ligand.

The physical form of the solid support depends on the particular mode of use of the binding member and on the physical form of the test device into which the binding member is incorporated. The solid support can be fabricated in thin, narrow strip form for use as a "dip stick," and this form is particularly adaptable to rapid printing procedures useful with the present invention. Wider strips of material such as microcrystalline cellulose can be useful for thin layer chromatographic procedures. The solid support can be provided in sheet form for use in some types of assays involving blotting from a previous chromatographic or electrophoretic separation, as in the well-known "Southern" or "Western" blotting techniques. These assays can involve immunochemical recognition or hybridization of complementary nucleic acids. Suitable materials for this type of solid support include paper or fabric.

Alternatively, the solid support can be placed on the inner surface of a vessel such as a test tube or centrifuge tube for use in immunochemical analyses requiring convenient separation of the test solution and the bound analyte. The solid support also can be fabricated in bead form for use in affinity chromatography, or incorporated on the surface of plates or slides for various types of quantitative immunoassays including single immunodiffusion, radial immunodiffusion, and rocket electrophoresis.

b. The Water-Soluble Polymer

The water-soluble polymer of the present invention can be capable of existence in two phases, a solution phase and a solid phase, and is capable of a readily reversible transition between these two phases before its incorporation into the binding member by fixation to the solid support. The polymer need not necessarily be capable of such a readily reversible transition after its incorporation into the binding member, but this capability is preferred, as it allows release of the polymer from the solid support. For simplicity, all polymers suitable for the binding member are hereinafter referred to as "reversibly soluble polymers" even though not capable of resolubilization after incorporation into the binding member.

Since many of the ligands such as enzymes and antibodies to be covalently attached to the polymer have a specific biological activity essential for the function of the ligand and are relatively labile molecules, it is preferred that the transition between the solution and solid phase occur under conditions preserving the stability and biological activity of any attached ligand. This usually rules out conditions for resolubilizing the polymer such as high temperature, extremely acid or alkaline conditions, or the addition of organic solvents or chaotropic agents such as guanidinium chloride or sodium dodecyl sulfate (SDS). These harsh conditions denature biological molecules such as proteins or nucleic acids by destroying their three-dimensional structures.

The reversibly soluble polymers of the present invention are capable of being covalently coupled to the ligand in the solution phase and are also capable of impregnating at least a portion of the micropores of the solid support in its solid phase.

The desirability of ready reversibility of the transition between the two phases of the polymer rules out most chemical polymerization reactions, which tend to be exothermic and effectively irreversible. In general, the reversibly soluble polymers of the present invention aggregate by non-covalent interactions, such as precipitation, flocculation, coagulation, or analogous reactions, triggered by an activating agent. Typically, the activating agent is a multivalent cation such as $Ca^{2+}$, which can cross-link individual molecules of the polymer by the formation of ionic bonds or salt links between the molecules. Alternatively, activation can be effected by a pH change. The reaction resulting in the transition of the polymer into the solid phase is referred to hereinafter generally as "cross-linking."

If addition of $Ca^{2+}$ ions initiates the transition to the solid phase, this can be reversed conveniently by the addition of a chelating agent. Typically, the chelating agent is ethylenediaminetetraacetic acid (EDTA) in concentrations sufficient to chelate all the calcium bound to the reversibly soluble polymer in its solid phase.

Examples of reversibly soluble polymers suitable for use with the present invention include alginic acid, carrageenan, pectin, pectic acid, and celluronic acid. Alginic acid is a natural product obtained from algae and is a polymer predominantly of mannuronic acid with possibly some guluronic acid. Carrageenan is also a natural product obtained from certain algae (Irish moss) and contains a sulfated polymer of galactose and anhydrogalactose. Pectin is isolated from apples and citrus fruits and consists of a polymer predominantly of galacturonic acid in which some of the carboxyl groups are esterified. Pectic acid is the free acid obtained by saponification of pectin. Celluronic acid is a polymer of glucuronic acid and glucose produced by controlled partial oxidation of cellulose with nitrogen dioxide. These acid polymers are generally used as their sodium salts.

c. The Covalently Attached Ligand (1) Ligands Usable in the Present Invention

The covalently attached ligand can be any ligand that is capable of attachment to the reversibly soluble polymer. The present invention is particularly useful for biologically active ligands such as antigens, antibodies, univalent antigen-binding fragments of antibodies, haptens, steroid or other hormones, receptors for hormones, physiologically active peptides, enzymes, or nucleic acids. However, biological activity is not a requirement for a ligand of the present invention and virtually any molecule that can be covalently attached to the polymer is a potential ligand. For example, aromatic amines such as fluoresceinamine can act as ligands.

Typically, carboxyl groups on the reversibly soluble polymer are activated with a coupling agent and coupled to hydroxyl or amino groups on the ligand. Alternatively, if the ligand contains carboxyl groups, it is also possible to couple carboxyl groups on the ligand to hydroxyl groups on the reversibly soluble polymer.

In most cases, the interaction or binding of the ligand to the analyte in the test sample must remain specific even after the ligand has been coupled to the reversibly soluble polymer to form a polymer-ligand conjugate. The nature of this specificity is discussed further under "Methods of Use of the Binding Member" below.

(2) Methods of Covalent Attachment of Ligand to Polymer

Several well-characterized methods of covalent attachment of the ligand to the reversibly soluble polymer are available, using a number of coupling agents.

(a) Carbodiimides

Carbodiimides are a group of compounds with the general formula R—N=C=N—R′, where R and R′ are aliphatic or aromatic. They act as condensing agents, linking an amino group with a carboxyl group to form a peptide bond by the elimination of water for the purposes of the present invention, the most useful carbodiimides are water-soluble carbodiimides such as 1-ethyl-3 3-dimethylaminopropyl) carbodiimide (DEC) and 1-cyclohexyl-3- [2-morpholinyl-4)ethyl] carbodiimide.

The carbodiimides can be used for the direct production of peptide bonds between an amino-group-containing ligand and a carboxyl-group-containing reversibly soluble polymer. All of the carbohydrate polymers discussed above under "The Reversibly Soluble Polymer" contain carboxyl groups suitable for activation by carbodiimides. All protein or peptide ligands contain suitable amino groups for coupling in the N-terminal amino group as well as the internal amino groups of lysine residues.

In the coupling by carbodiimide, first the carboxyl-containing component is activated, and then the amino-containing component is introduced into the reaction. For example, as described in greater detail below in Example 1, if the reversibly soluble polymer is sodium alginate and the ligand is a protein ligand such as human chorionic gonadotropin (hCG) or monoclonal antibody to hCG, the reaction proceeds efficiently if 100 mg of DEC is added to 20 ml of an 0.5% solution of sodium alginate in 0.05 M NaCl at pH 4.7. The reaction of the DEC with the alginate is allowed to proceed for 2 minutes, and then one-quarter volume of the ligand at a concentration between 2.0 and 10.0 mg/ml in 0.05 M NaCl, 0.1 M NaHCO$_3$, pH 9.0, is added to the activated alginate. The reaction is allowed to proceed overnight at 4°, and the conjugate is purified by size exclusion chromatography on a suitable gel filtration column such as SEPHACRYL (TM) S-300.

(b) Carbonyldiimidazole

The reagent carbonyldiimidazole (CDI), more accurately 1,1′-carbonyldiimidazole, is widely used for the formation of ester linkages by condensation. In the present invention, carbonyldiimidazole can be used to couple carboxyl group-containing ligands to the hydroxyls of sugar groups. A method suitable for the production of steroid-BSA conjugates for use in immunoassay has been described by W. A. Colburn, "Radioimmunoassay for Fluoxymesterone Halotestin (R))," *Steroids* 25, 43–52 (1975). A steroid derivatized to a carboxymethoxime to incorporate the necessary carboxyl group for the conjugation reaction was conjugated to bovine serum albumin (BSA). 0.3 mole each of the steroid and CDI were dissolved in 1 ml of dimethylformamide (DMF) under reduced pressure. 0.003 mole of BSA was then dissolved in 1.5 ml of water, and the DMF solution was added dropwise to the aqueous solution while mixing. The mixture was then adjusted to pH 9.0 with 0 1 M NaOH before more DMF was added to clear the solution. Only part of the mixture was solubilized by this procedure. After dialysis, the cloudy solution was filtered. The filtrate was air dried and the soluble portion freeze dried. In the conjugated product, approximately 38 moles of steroid were coupled per mole of BSA.

(c) Cyanogen Bromide

Cyanogen bromide, CNBr, is an effective coupling agent. It is generally used to activate hydroxyl groups for coupling to amino groups, producing an isourea linkage, $—O—C(NH_2)^{30}—NHR$. In the present invention, CNBr can be used to activate hydroxyl groups on the sugars of the reversibly soluble polymer for coupling to amino groups on the ligand.

(d) Other Coupling Methods

There are a large number of other coupling methods and reagents for covalently coupling the ligand to the reversibly soluble polymer. These methods and reagents include:

(i) The Mixed Anhydride Method

In the mixed anhydride method, the reversibly soluble polymer containing carboxyl groups on the sugars is reacted with ethyl chloroformate in the presence of triethylamine to produce a mixed anhydride. The mixed anhydride is then reacted with a ligand having either basic amino or phenolic hydroxyl groups to form amide or ester linkages, respectively.

(ii) Reaction with N-Hydroxypiperidine

In this method, the reversibly soluble polymer containing carboxyl groups on the sugars is reacted with N-hydroxypiperidine in the presence of N,N′-dicyclohexylcarbodiimide to produce the N-hydroxypiperidine ester of the reversibly soluble polymer. This ester is the reacted with the ligand to produce amide or possibly ester linkages between the polymer and the ligand with the release of N-hydroxypiperidine.

(iii) Reaction with Hydrazine Hydrate

In this method, a reversibly soluble polymer whose carboxyl group are partially esterified, such as pectin, is reacted with hydrazine hydrate with formation of the corresponding hydrazide. This hydrazide is then treated with HNO$_2$ to produce the corresponding azide. The azide is then reacted with the ligand which then becomes linked to the reversibly soluble polymer via amide or ester linkages.

(iv) p-Benzoquinone

The reagent p-benzoquinone can be used to crosslink a protein ligand to a reversibly soluble polymer containing polysaccharide. The reaction occurs in two steps: the first step involves reaction of the protein ligand with the benzoquinone reagent at pH 6.0 and the second step involves the reaction of the complex formed in the first step with the reversibly soluble polymer at pH 8.0 to form a conjugate.

Still other crosslinking methods can be appropriate depending on the nature of the ligand and the reversibly soluble polymer. In some cases, it can be desirable to add a spacer or bridging molecule between the reversibly soluble polymer and the ligand in order to eliminate steric hindrance between the analyte and the reversibly soluble polymer when the analyte binds the ligand.

2. Methods of Preparation of the Binding Member

The basic procedure for preparing the binding member is relatively straightforward and comprises three steps.

The first step comprises covalently coupling a ligand to a suitable polymer in solution to form a ligand-polymer conjugate. The polymer is capable of reversible transition between a solid phase and a solution phase before being fixed to a solid support. This coupling generally takes place under conditions that do not adversely affect the stability or biological activity of the ligand. For man labile ligands, especially protein ligands, this requires that the coupling reaction be performed in aqueous solution and at room temperature or below. Details of various coupling procedures useful for the production of polymer-ligand conjugates are given above under "Methods of Covalent Attachment."

The second step comprises impregnating the solid support with the polymer-ligand conjugate. This can be done manually for some small-scale applications by spreading the polymer-ligand conjugate on top of the support and allowing the conjugate to impregnate the micropores of the support. For larger-scale applications, this impregnation step is preferably performed on automated equipment. A printing press useful for printing on paper, such as a flexopress, can be used, with the solid support being impregnated while on the printing press. For example, a doctor blade and roller can be used to spread the liquid-polymer conjugate on the solid support.

The third step comprises cross-linking the liquid-polymer conjugate. This step can occur directly on the printing press by application of a calcium salt to the solid support impregnated with the conjugate. Alternatively, the step of cross-linking the ligand-polymer conjugate can occur later, such as during the performance of the assay. In this alternative, the polymer-ligand conjugate can be applied to the solid support in a liquid state and then allowed to dry without cross-linking the polymer. The polymer is sufficiently stable in this dry, but uncross-linked state, to allow storage of the assay member. The polymer is then cross-linked during the subsequent enzymatic or immunochemical reaction, which takes place in a buffer containing calcium or other divalent cation that can cause cross-linking. Cross-linking the ligand-polymer conjugate preferably occurs rapidly; if it occurs on the printing press and automated printing equipment is used, it most preferably occurs in less than about one second after initiation of cross-linking.

When this general method is used for a rapid process for producing a test strip on a printing press, an additional step is generally necessary before the impregnating step and after the step of covalently coupling the ligand to the polymer. This additional step comprises placing the ligand-polymer conjugate into a suspension suitable for printing onto a solid support using the high-speed printing press. Optimally, when test strips are produced on such a printing press, the step of cross-linking the water-soluble polymer occurs simultaneously with the step of impregnating the solid support with the conjugate on the printing press and is completed within about one second after it is initiated.

If the polymer is not already in solution, a preliminary step can comprise the solubilization of the polymer. This is preferably done in a buffer suitable for the subsequent coupling reaction and that is free of $Ca^{2+}$ or other divalent cations that could cause the transition of the polymer back into the solid phase or premature cross-linking.

3. Methods of Use of the Binding Member a. Nature of the Analyte and the Test Sample

In general, the analyte is a substance specifically bound to the ligand. The terms "specifically bound" or "specifically interacting" refer to an interaction comparable in strength and specificity to the interaction between an enzyme and its substrate or an antibody and its antigen. These interactions are relatively precise short-range noncovalent interactions mediated by forces such as hydrogen bonding, ionic bonding, and van der Waals bonding, and sensitive to relatively small differences in structure of one of the interacting components. Some other examples of interactions meeting this criterion include hybridization between a single-stranded DNA molecule and a complementary DNA or RNA molecule, the interaction between protein A from *Staphylococcus aureus* and the Fc fragment of IgG, the interaction between biotin and avidin, and the binding of hormones to their receptors.

Typical examples of ligands and analytes are given below in Table 1. These examples are illustrative only and are not meant to exhaust the possible useful combinations of ligand and analyte.

TABLE 1

EXAMPLES OF LIGANDS AND ANALYTES BINDING TO THOSE LIGANDS

| Ligand | Analyte Binding to Ligand |
| --- | --- |
| Antibody | Antigen |
| Univalent Antibody Fragment | Antigen |
| Antigen | Antibody |
| Hapten | Antibody |
| Substrate | Enzyme |
| Substrate Analogue | Enzyme |
| Inhibitor | Enzyme |
| Enzyme | Substrate |
| Enzyme | Inhibitor |
| Hormone Receptor | Hormone |
| Hormone | Hormone Receptor |
| Single-Stranded Nucleic Acid | Complementary Single-Stranded Nucleic Acid |

The test sample is basically anY aqueous fluid which contains or might contain an analyte and which is compatible with the stability of the binding member. Typical examples of test samples include blood; blood fractions such as plasma or serum; urine; saliva; semen; extraction liquid from a swab; and cerebrospinal fluid (CSF). The quantity of test sample used is a quantity sufficient to ensure that the surface area of the binding member can be placed in contact with the test sample.

b. Incorporation of the Binding Member into a Test Device

For actual use in detection of any analyte in a test sample, the binding member of the present invention is typically incorporated into a test device.

The present invention is particularly adapted for use with in a test device in the form of a "dip stick" or test strip. When the test device is in that form, the test device actually used is simply the binding member itself.

In other cases, such as when the assay member is incorporated as part of a hollow vessel such as a test tube or a centrifuge tube, the entire vessel forms the test device which can be used for various types of immunoassays or binding assays. The binding member is incorporated as part of the inner liquid-contacting surface of the vessel. This configuration of the binding member and test device can allow the quantitative recovery of the analyte binding to the ligand simply by resolubilizing the reversibly soluble polymer, using conditions under which the ligand is separated from the analyte by the weakening of the specific ligand-analyte interactions. Such conditions can include the use of high concentrations of salt, such as 1.0 M NaCl or KCl, or a detergent such as sodium dodecyl sulfate SDS). The analyte can then be conveniently separated from the resolubilized polymer by such techniques as gel filtration or reprecipitation of the polymer under conditions where ligand-analyte interactions are eliminated. In some cases, it can also be possible to recover the analyte binding to the ligand without resolubilizing the polymer if the ligand-analyte interactions can be sufficiently weakened.

Other forms of test device into which the assay member of the present invention can be incorporated include slides and beads. Slides are useful for various types of quantitative immunoassays, including single immunodiffusion, radial immunodiffusion, and rocket electrophoresis. All of these procedures as generally performed require the uniform incorporation of antibody into a matrix generally of agar. In preparing the test device for such assays, the assay member to which the appropriate antibody is attached is placed on slides in gel form and appropriate holes are punched in the gel for placement of the antigen. Beads such as agarose are useful as test devices for procedures such as affinity chromatography.

c. Assay Schemes for Detecting Analytes

Several assay schemes for analytes specifically binding, directly or indirectly, the ligand of the solid phase binding member are available. When the analyte binds the ligand directly, these assay schemes follow the general pattern of:

(1) binding the analyte to the solid phase binding member, the binding occurring in the test sample into which the binding member is placed;

(2) removing the binding member from the test solution and washing the binding member, thereby separating analyte bound to the binding member from any unbound analyte; and (3) determining the presence of the analyte bound to the binding member.

In this process, the reversibly soluble polymer is in its solid phase and physically attached to the solid support during the first two steps. The polymer can be resolubilized when determining the presence of the analyte bound to the binding member so that bound analyte can be recovered free of the ligand and the solid support for determination. Determination of the analyte bound to the assay member can be a simple qualitative determination of the presence or absence of the analyte. Preferably, analyte is quantitatively determined.

One method of determining the presence of analyte bound to the binding member is to react the washed binding member with a signal producing system. When analyte is bound to the binding member, the signal producing system produces a detectable product that also binds to the binding member. The detectable product can be visually detectable, detectable by ultraviolet spectrophotometry or detectable by the measurement of radioactivity.

The signal producing system in this arrangement can include an enzyme capable of catalyzing oxidation-reduction ("redox") reactions. Several such enzymes are useful in producing such detectable products. For example, the enzyme horseradish peroxidase can produce colored oxidized products from such substrates as o-dianisidine or 4-chloro-1-naphthol by catalyzing their oxidation with $H_2O_2$. The $H_2O_2$ can be produced by the oxidation of glucose with molecular oxygen, catalyzed by the enzyme glucose oxidase. Glucose oxidase itself can be useful in the production of visually detectable products. For example, the enzyme can catalyze electron transfer between m-phenazine methosulfate and t-nitroblue tetrazolium chloride to produce a reduced insoluble colored formazan product from the tetrazolium.

Preferably, there is a sufficient quantity of the polymer and the ligand bound to the support that substantially all analyte normally found in the test sample and capable of binding to the ligand is bound. Here, the term "normally" not only encompasses those concentrations of analyte found in healthy individuals, but also those concentrations found in disease states. For example, if the analyte is glucose in a test sample of serum, healthy individuals generally have values of from 70 mg to 105 mg of glucose per 100 ml of serum, but these values can be increased several fold in severe cases of diabetes. A binding member for the determination of glucose and incorporating the glucose-specific enzyme glucose oxidase as ligand must be able to bind even the elevated quantities of glucose for accuracy in clinical use.

Alternatively, the analyte can interact with the ligand indirectly. In this indirect arrangement, the analyte can bind to a second moiety incorporated in the test device but not immobilized. This second moiety can be a mobile labeled antibody. In this arrangement, the ligand can be an immobilized analyte or analyte analog capable of reacting with the mobile labeled antibody. The analyte and ligand effectively compete for the mobile labeled antibody.

This discussion of possible assay schemes is not exclusive, and many other arrangements are possible and usable with the binding member of the present invention, depending on the nature of the analyte and the ligand.

EXAMPLES

EXAMPLE 1

Covalent Attachment of Protein and Non-Protein Ligands to Sodium Alginate Using 1-Ethyl-3-3-Dimethylaminopropyl Carbodiimide Reagent The protein ligands used in this example included human chorionic gonadotropin (hCG) and monoclonal antibody to hCG. The nonprotein ligand used was fluoresceinamine.

For the proteins, the ligands to be coupled were dialyzed in three changes of a buffer solution of 0.05 M NaCl, 0.1 M NaHCO$_3$, pH 9.0. The volume of each change of buffer used was 40 times the volume of ligand solution. Fluoresceinamine, as a low-molecular-weight molecule not suitable for dialysis, was dissolved directly in the same NaCl-NaHCO$_3$ buffer. The concentration of the ligand in the solution was adjusted to be between 2.0 and 10.0 mg of ligand per milliliter for the subsequent conjugation reaction.

Sodium alginate was dissolved at a concentration of 1% (w/v) and dialyzed in three changes of 0.05 M NaCl, pH 4.7. The volume of each change of buffer used was 40 times the volume of ligand solution. After dialysis, the alginate was diluted to 0.5% with the same buffer used for dialysis. The ligands to be coupled to the alginate were recovered from dialysis, their concentrations adjusted if necessary, and filtered through an nitrocellulose membrane filter with a pore diameter of 0.2 μm. A small amount of such ligand was retained for later analysis. For each ligand, 20 milliliters of 0.5% sodium alginate were placed in a beaker to allow monitoring of the pH. The contents of the beaker were stirred and the pH of the solution was adjusted to 4.7 with either 0.1 N HCl or 0.1 N NaOH as required. One hundred milligrams of 1-ethyl-3-(3-dimethylaminopropyl] carbodiimide (DEC) was slowly dispersed into the stirring sodium alginate solution. The reaction of the DEC with the sodium alginate was allowed to proceed for 2 minutes with maintenance of the pH at 4.7. The ligand solution and the solution of activated sodium alginate were combined at a ratio of 0.5 ml of ligand solution to 2.0 ml of activated sodium alginate solution. The reaction was then allowed to continue on a rocker at 4° C. overnight. The product was then purified by size exclusion chromatography on a suitable column of SEPHACRYL l(TM) S-300 in an isocratic (constant salt concentration) system of 0.012 M Tris, 0.12 M glycine pH 8.0, 0.01 M EDTA. The conjugated product was concentrated in an Amicon stir cell under $N_2$ gas using a membrane with a molecular weight cutoff of 10,000 daltons. The concentrated conjugate was dialyzed in an appropriate buffer for the stability of the conjugate.

Chromatographic analysis of the conjugated product, hCG-alginate, was carried out using a Superose 12 size exclusion column. For comparison, similar chromatography was carried out on the same quantity of non-DEC-treated alginate combined with hCG. The concentration of hCG in the original ligand solution was estimated by an $A_{280}$ measurement on a Beckman DU7 spectrophotometer using a quartz cuvette with a 1 cm path length. The estimated concentration of hCG in the original solution was determined to be 2.22 $A_{280}$ units/ml. The chromatographic analysis resulted in two fractions, a rapidly-eluting peak representing the alginate and a more slowly-eluting peak representing free hCG. The alginate was quantitated by measuring its refractive index change, while hCG was quantitated by measuring its $A_{280}$. Comparison of the two chromatograms showed that there was no significant difference in the amount of sodium alginate for DEC-treated versus non-DEC-treated material. However, there was about a 1.6-fold increase in the amount of hCG associated with the main alginate peak for DEC-treated material as compared with non-DEC-treated material. There was a corresponding 1.4-fold decrease in the amount of hCG found in the free hCG peak for the DEC-treated material compared with the non-DEC-treated material.

Similar results were obtained from chromatographic analysis on the conjugates of the monoclonal antibody to hCG and fluoresceinamine with sodium alginate.

The hCG coupled in the conjugate was shown to maintain its ability to be recognized by two different antibodies in a double antibody sandwich assay, while the coupled monoclonal antibody was similarly shown to bind hCG on a coated plate and be bound by a second antibody in an immunoassay system.

These results demonstrate that it is quite feasible to covalently attach several different protein and nonprotein ligands to sodium alginate, and that the biological activity of such proteins is maintained after such attachment.

EXAMPLE 2

Immobilization of Human Chorionic Gonadotropin on a Porous Matrix via a Calcium-Dependent Insolubilization of Human Chorionic Gonadotropin-Alginate Conjugate on Ravon Rayon material #8S rayon from Schleicher & Schuell) was cut into strips with dimensions of 0.6 cm in width and 7.5 cm in length Using a jig with a pointed end, points were cut in one end of each strip that were made on a flexopress. The rayon strips were prewashed in 0.05 M Tris pH 7.5, 0.155 M NaCl by eluting the buffer through the rayon strips by capillary action and gravity flow, using 1.0 ml of buffer per strip. The strips were then allowed to air dry Ten microliters of hCG-alginate conjugate as prepared in Example 1 were then spotted without dilution on the center of the prewashed strips about 5.0 cm from the unpointed end of the strip, and then allowed to air dry. Two chromatographic fractions from the conjugate preparation of Example 1 were kept separate, and thus Fractions 1 and 2 of the conjugate were tested individually. One milliliter each of Fraction 1 and Fraction 2 was spiked with 20 μl of 1% alginate solution to raise the alginate concentration. The following controls were used: (a) Tris-NaCl buffer without alginate or hCG; (b) 200 mg/ml of unreacted alginate; and (c) 200 mg/ml of hCG and 200 mg/ml of unreacted alginate. Duplicate strips for each solution were used. The strips were aerosoled with 0.05 M Tris-HCl pH 7.5, 0.155 M NaCl, 0.2 M CaCl, and then allowed to air dry overnight. After being allowed to dry, the strips were eluted by capillary action and gravity flow by wicking the unpointed end of the strips into a reservoir containing the same Tris-NaCl-CaCl, buffer used to aerosol the strips. The eluate was collected into ten separate microtiter plate wells per strip at 5 minutes per fraction. This gave fraction volumes of approximately 120 μl. After this first washing in calcium-containing buffer, the strips were again allowed to air dry. The strips were then eluted by the same procedure in a buffer containing 0.05 M Tris-HCl pH 7.5, 0.155 M NaCl, 0.05 M EDTA to release bound alginate and hCG. The alginate and hCG contents of each fraction from both the first $CaCl_2$ wash and the second EDTA elution were determined. Alginate content was determined by a colorimetric assay using iron salts after degradation of the alginate with acid. The hCG content was determined using a double antibody sandwich enzyme immunoassay (EIA) for hCG. The absorbance values obtained in the alginate and hCG assays were converted to quantities of alginate and hCG in micrograms by running a calibration curve of known standards on the same plate. Assays for hCG were performed only on hCG-containing strips only. Previously hCG assays had been done on blank strips and alginate spotted strips and had been found not to yield any nonspecific signal when no hCG had been present.

The blank control using a strip with only Tris-NaCl buffer deposited gave only background values for the alginate assay. The alginate control verified what had been previously observed in Example 1, demonstrating that sodium alginate can be immobilized on rayon in a calcium-dependent fashion and subsequently removed by chelation of the calcium ions by EDTA. Results of the assays on the non-activated alginate-hCG mixture showed that hCG eluted in fractions 1 and 2 of the $CaCl_2$ wash with some residual hCG eluting in the EDTA eluate. At least 75 percent of the hCG eluted in the CACl2 wash. This showed, as expected, that hCG did not attach to non-activated alginate. The elution profiles for the Fraction 1 and Fraction 2 hCG-alginate conjugates, tested separately, each showed little or no hCG eluting in the CaCl2 wash. The bulk of the hCG placed on the strips, at least 90 percent, eluted in the first few fractions of the EDTA eluate associated with the previously immobilized alginate. Somewhat more hCG was bound in Fraction 2 of the hCG -alginate conjugate than in Fraction 1. An alternative explanation of this last finding is that there was more hCG available for binding in the hCG assay for the Fraction 2 conjugate than for the Fraction 1 conjugate.

This example shows that sodium alginate and two separate fractions of hCG-alginate can be immobilized on rayon in a calcium-dependent fashion. The reversibility of the immobilization was also demonstrated when the eluting conditions were changed from calcium-containing to EDTA-containing eluting buffer.

EXAMPLE 3

Demonstration of Increased Binding of Anti-Human Chorionic Gonadotropin-Horseradish Peroxidase Conjugate to Human Chorionic Gonadotropin-Alginate on Rayon Pointed 0.6 cm ×7.5 cm rayon strips were prewashed by eluting 0.05 M Tris-HCl pH 7.5, 0.155 M NaCl through the strips by capillary action and gravity flow. Each strip was washed with about 1.0 ml of buffer and allowed to air dry. Ten microliters of hCG-alginate conjugate as prepared in Example 1 and used in Example 2 were spotted onto the center of each of the rayon strips about 5.0 cm from the unpointed end. Both Fraction 1 and Fraction 2 as used in Example 2 were spotted undiluted onto the rayon strips. The controls included; (a) Tris-NaCl buffer; (b) 500 mg/ml of unactivated alginate; and (c) 500 mg/ml of activated alginate blocked with glycine and without hCG. Duplicate strips for each solution were used. The strips were aerosoled with 0.05 M Tris-HCl pH 7.5, 0.155 M NaCl, 0.2 M CaCl2, and then allowed to dry overnight. A conjugate of anti-hCG antibody and horseradish peroxidase that had been prepared previously was diluted 1:5000 in the same calcium-containing buffer. Twenty-five milliliters of diluted conjugate was placed into each of two plastic weighing boats, and one set of duplicate strips was immersed in each weighing boat for 30 minutes. The strips were then removed and allowed to air dry for one hour. Unbound antibody-enzyme conjugate was washed from the strips by eluting the strips in the same buffer used to dilute the conjugate, with no conjugate present. Six successive fractions were collected for five minutes each into microtiter plates by the same procedure used in Example 2. Bound antibody-enzyme conjugate was then released by eluting the strips with 0.05 M Tris-HCl pH 7.5, 0.155 M NaCl, 0.05 M EDTA. with six successive fractions again being collected for five minutes each. The contents of each fraction from the $CaCl_2$-containing wash and the EDTA containing buffer eluate were assayed for the presence of active peroxidase by placing 25.0 μl of each fraction to be tested in the bottom of a microtiter plate well. On top of these samples was pipetted 200 μl of a standard color-forming reagent for horseradish peroxidase using 3,3',5,5'-tetramethylbenzidine (TMB). The amount of color formed, as determined by measured $A_{660}$, is proportional to the amount of active enzyme present in the fraction. The average $A_{660}$ in the assay of the various EDTA eluates is given in Table 2.

When comparing the yield of bound antibody-enzyme conjugate as shown in Table 2, there was a significant difference between the Fraction 1 and Fraction 2 hCG-alginate conjugates and the three control samples. It also appeared that Fraction 2 binds more antibody-enzyme conjugate than did Fraction 1. This difference is consistent with the results in Example 2 which showed that Fraction 2 contains more measurable hCG associated with the alginate than Fraction 1.

This example shows that an hCG-alginate conjugate immobilized on rayon can bind an anti-hCG-horseradish peroxidase conjugate. The presence of such binding is crucial for the use of such alginate conjugates in the production of the binding members of the present invention.

TABLE 2

BINDING OF ANTI-HUMAN CHORIONIC GONADOTROPIN-HORSERADISH PEROXIDASE CONJUGATE TO HUMAN CHORIONIC GONADOTROPIN-ALGINATE CONJUGATE IMMOBILIZED ON RAYON STRIP (EXAMPLE 3)

| Sample on Rayon Strip | Average $A_{660}$ Produced in Peroxidase Assay |
|---|---|
| Blank (Buffer Only) | 0.062 |
| Non-Activated Alginate | 0.042 |
| Activated and Blocked Alginate | 0.082 |
| Alginate-hCG Conjugate Fraction 1 | 0.136 |
| Alginate-hCG Conjugate Fraction 2 | 0.215 |

The $A_{660}$ produced from TMB in the peroxidase assay is a measure of the amount of active peroxidase binding to the strip. Samples were run in duplicate.

The binding member of the present invention meets the needs previously set forth: rapidity of binding, low cost, usefulness with a wide variety of ligands and solid supports, preservation of the stability and biological activity of the ligand, suitability for use with rapid methods of printing, and production of a stable product.

The cross-linking of the reversibly soluble polymer of the present invention occurs very rapidly and under conditions wherein the covalently bound ligand can readily retain its structure and activity. These conditions also favor the stability of the conjugated product. The rapidity of this cross-linking makes the method of the present invention suitable for use in conjunction with automated high-speed printing methods.

In this method, there is no need to bind the ligand covalently to the solid support. The step of covalently binding the ligand to the solid support is technically difficult, time-consuming, and expensive to perform. The elimination of that step in the present invention greatly reduces the cost of preparing such bound ligands, and makes the process usable with a wider variety of ligands and solid supports. Since the coupling reaction of the present invention couples the ligand to a carbohydrate polymer, conditions for the coupling reaction can be more readily chosen to preserve the activity of the ligand. If the ligand were to be covalently coupled to the solid support, more drastic coupling conditions would often be needed, which could denature or inactivate the ligand., The covalent coupling of the ligand to the reversibly soluble polymer also gives several important advantages over procedures using a mere entrapment or physical association of the ligand and the polymer. Covalent coupling preserves the association of the ligand and the polymer in both the solid and the liquid phase. It prevents a portion of the ligand from leaching out of the polymer during the reaction with the analyte in the test sample. This leaching out of the ligand can lower the reaction rate between the analyte and ligand and can complicate the analysis of the results of analyte binding by the ligand, because the effective concentration of the ligand would be decreasing with time during the course of the reaction. This absence of the leaching effect also allows a lower concentration of ligand than would otherwise be required were the ligand not covalently coupled. This lower concentration of the ligand can be important in preventing undesirable steric hindrance and excluded volume effects, especially for larger ligands such as intact antibody molecules.

The absence of the need to entrap the ligand physically in the polymer also allows the use of a lower concentration of polymer than would otherwise be necessary in methods not using covalent coupling. This saves material and also facilitates the reaction between the ligand and the analyte by allowing more ready access of the analyte to the ligand.

Although the present invention has been described in considerable detail with regard to certain preferred versions thereof other versions are possible. Therefore the spirit and scope of the appended claims should not be limited to the description of the preferred versions contained herein.

What is claimed is:

1. A solid phase binding member for an analyte in an aqueous test sample, the binding member comprising:
   (a) a solid support having micropores; and
   (b) a ligand covalently attached to a water-soluble polymer, wherein:
      (i) the polymer is in a solid phase aggregated by noncovalent interactions and impregnates at least a portion of the micropores of the solid support without covalent binding between the polymer and the support, the impregnation occurring in such manner that the test sample can penetrate the micropores of the solid support impregnated with the polymer, the polymer having been aggregated from a solution phase into the solid phase under conditions not denaturing the ligand; and
      (ii) the ligand is capable of interacting, directly or indirectly, so as to specifically bind with the analyte.

2. The binding member of claim 1 wherein the solid support has micropores throughout its entire structure, the micropores penetrating through the entire solid support.

3. The binding member of claim 1 wherein the solid support has micropores only on its surface.

4. The binding member of claim 1 wherein the weight of the polymer per unit of surface area of the external surface of the solid support is no greater than about 0.01 g of polymer per square centimeter of surface area of the external surface of the solid support.

5. The binding member of claim 1 wherein the weight of the polymer per unit of surface area of the external surface of the solid support is no greater than about 0.002 g of polymer per square centimeter of surface area of the external surface of the solid support.

6. The binding member of claim 2 wherein the solid support is selected from the group consisting of rayon, paper, non-rayon fabric, plastic, agarose beads, polyacrylamide beads, glass, and microcrystalline cellulose.

7. The binding member of claim 3 wherein the solid support is selected from the group consisting of acid-treated polycarbonate plastic and fritted glass.

8. The binding member of claim 1 prepared by cross-linking the polymer together when the polymer impregnates the micropores of the support.

9. The binding member of claim 8 wherein the concentration of the polymer in solution prior to cross-linking is less than about 1% by weight.

10. The binding member of claim 8 wherein the concentration of the polymer in solution prior to cross-linking is less than about 0.5% by weight.

11. The binding member of claim 8 wherein the concentration of the polymer in solution prior to cross-linking is greater than about 0.2% by weight.

12. The binding member of claim 1 wherein the polymer is sodium alginate.

13. The binding member of claim 1 wherein the polymer is carrageenan.

14. The binding member of claim 1 wherein the transition of the polymer from the solid phase to the solution phase occurs readily at a temperature of about 25° C. or less.

15. The binding member of claim 1 wherein the ligand contains amino groups and the polymer contains carboxyl groups, the coupling of the ligand to the polymer occurring by reaction of the amino groups on the ligand and the carboxyl groups on the polymer with 1-ethyl-3-(3-dimethylaminopropyl) carbodiimide.

16. The binding member of claim 1 wherein the ligand contains carboxyl groups and the polymer contains hydroxyl groups, the coupling of the ligand to the polymer occurring by reaction of the carboxyl groups on the ligand and the hydroxyl groups on the polymer with carbonyldiimidazole.

17. The binding member of claim 1 wherein the ligand contains amino groups and the polymer contains hydroxyl groups, the coupling of the ligand to the polymer occurring by reaction of the amino groups on the ligand and the hydroxyl groups on the polymer with cyanogen bromide.

18. A solid phase binding member for an analyte in an aqueous test sample, the binding member comprising:
   (a) a solid support having micropores; and
   (b) a ligand covalently attached to a water-soluble polymer, wherein:
      (i) the polymer is in a solid phase aggregated by noncovalent interactions and impregnates at least a portion of the micropores of the solid support without covalent binding between the polymer and the support, the impregnation occurring in such manner that the test sample can penetrate the micropores of the solid support impregnated with the polymer, the polymer having been aggregated from a solution phase into the solid phase under conditions not denaturing the ligand and being capable of a transition from the solid phase to the solution phase after its impregnation of the micropores of the solid support; and
      (ii) the ligand is capable of interacting, directly or indirectly, so as to specifically bind with the analyte.

19. A solid phase binding member for an analyte in an aqueous test sample, the binding member comprising:
   (a) a solid support having micropores; and
   (b) a biologically active ligand covalently attached to a water-soluble polymer, wherein:

(i) the polymer is in a solid phase aggregated by noncovalent interactions and impregnates at least a portion of the micropores of the solid support without covalent binding between the polymer and the support, the impregnation occurring in such manner that the test sample can penetrate the micropores of the solid support impregnated with the polymer, the polymer having been aggregated from a solution phase into the solid phase under conditions not denaturing the ligand; and (ii) the biologically active ligand is capable of interacting, directly or indirectly, so as to specifically bind with the analyte.

20. A solid phase binding member for an analyte in an aqueous test sample, the binding member comprising:
(a) a solid support having micropores; and
(b) a biologically active ligand covalently attached to a water-soluble polymer, wherein:
(i) the polymer is in a solid phase aggregated by noncovalent interactions and impregnates at least a portion of the micropores of the solid support without covalent binding between the polymer and the support, the impregnation occurring in such manner that the test sample can penetrate the micropores of the solid support impregnated with the polymer, the polymer having been aggregated from a solution phase into the solid phase under conditions not denaturing the ligand; and
(ii) the biologically active ligand is capable of interacting, directly or indirectly, so as to specifically bind with the analyte, the transition of the polymer from the solution phase to the solid phase being reversible under conditions preserving the biological activity of the ligand through both the transition from the solution phase to the solid phase and the transition from the solid phase to the solution phase.

21. The binding member of claim 19 wherein the ligand is an antibody.

22. The binding member of claim 19 wherein the ligand is a univalent antigen-binding fragment of an antibody.

23. The binding member of claim 19 wherein the ligand is an antigen.

24. The binding member of claim 19 wherein the ligand is a hapten.

25. The binding member of claim 19 wherein the ligand is an enzyme.

26. The binding member of claim 19 wherein the ligand is a hormone.

27. The binding member of claim 19 wherein the ligand is a receptor for a hormone.

28. The binding member of claim 19 wherein the ligand is a single-stranded nucleic acid.

29. An apparatus for detecting an analyte in a test sample wherein the binding member of claim 1, 18, 19, or 20 is incorporated into a test device in the form of a dip stick.

30. An apparatus for detecting an analyte in a test sample wherein the binding member of claim 1, 18, 19, or 20 is incorporated on an inner liquid-contacting surface of a test device in the form of a vessel.

31. An apparatus for detecting an analyte in a test sample wherein the binding member of claim 1, 18, 19, or 20 is incorporated on the surface of a test device in the form of a microscope slide.

32. An apparatus for detecting an analyte in a test sample wherein the binding member of claim 1, 18, 19, or 20 is incorporated into a test device in the form of a bead.

33. A process for producing a solid phase binding member for an analyte in an aqueous test sample, the process comprising the steps of:
(a) covalently coupling a ligand to a water-soluble polymer in solution, the polymer being capable of a reversible transition between a solid phase aggregated by noncovalent interactions and a solution phase in either direction before the polymer is fixed to a solid support, the covalent coupling of the ligand to the polymer producing a ligand-polymer conjugate;
(b) impregnating at least a portion of a solid support having micropores with the ligand-polymer conjugate; and
(c) cross-linking the polymer such that the ligand-polymer conjugate is noncovalently fixed to the solid support.

34. The process of claim 33 wherein the step of cross-linking the polymer comprises introducing $Ca^{2+}$ ions in solution to the surface of the solid support.

35. The process of claim 33 wherein the step of impregnating the solid support with the conjugate comprises applying the conjugate to the solid support on a printing press.

36. The process of claim 35 wherein the step of applying the conjugate to the solid support on the printing press is performed with a doctor blade and roller.

37. The process of claim 33 wherein the step of cross-linking polymer occurs simultaneously with the step of impregnating the solid support with the conjugate.

38. The process of claim 33 wherein the step of cross-linking the polymer occurs after the step of impregnating the solid support with the conjugate.

39. The process of claim 38 wherein the polymer is allowed to dry after the step of impregnating the solid support with the conjugate and before the step of cross-linking the polymer.

40. The process of claim 33 wherein the polymer in solution of step (a) is produced by solubulizing a water-soluble polymer in its solid phase.

41. The process of claim 33 wherein the step of cross-linking the polymer is completed within about one second after it is initiated.

42. A process for producing a test strip on a printing press, comprising the steps of:
(a) covalently coupling a ligand to a water-soluble polymer in solution, the polymer being capable of a reversible transition between a solid phase aggregated by noncovalent interactions and a solution phase in either direction before being fixed to a solid support, the covalent coupling of the ligand to the polymer producing a ligand-polymer conjugate;
(b) placing the ligand-polymer conjugate into a suspension suitable for printing onto the solid support using the printing press;
(c) impregnating at least a portion of a solid support having micropores with the ligand-polymer conjugate by printing the suspension containing the conjugate onto the solid support using the printing press; and
(d) cross-linking the polymer such that the ligand-polymer conjugate is noncovalently fixed to the solid support to form the test strip, the step of cross-linking being completed within less than about one second after being initiated and occurring substantially simultaneously with the step of impregnating the solid support with the conjugate.

43. A method for detecting an analyte in an aqueous test sample, the analyte specifically binding to a ligand of a solid phase binding member, the method comprising the steps of:
(a) binding the analyte to the solid phase binding member, the binding occurring in the test sample into which the binding member is placed, the binding member comprising:
(i) a solid support having micropores; and
(ii) a ligand covalently attached to a water-soluble polymer, wherein:
(A) the polymer is reversibly water-soluble before its application to the solid support, the polymer being in its solid phase aggregated by noncovalent interactions and impregnates at least a portion of the micropores of the solid support in such manner that the test sample can penetrate the micropores of the solid support impregnated noncovalently with the polymer; and
(B) the ligand is capable of interacting, directly or indirectly, so as to specifically bind with the analyte;
(b) removing the binding member from the test sample and washing the binding member, thereby separating analyte bound to the binding member from unbound analyte;
(c) resolubilizing the reversibly water-soluble polymer in such a manner that interactions between the ligand and the analyte are weakened so that previously bound analyte can be recovered free of the ligand and solid support for determination;
(d) recovering the previously bound analyte free of the ligand and the solid support; and
(e) then determining the presence of the recovered analyte.

44. A method for detecting an analyte in an aqueous test sample, the analyte specifically binding to a ligand of a solid phase binding member, the method comprising the steps of:
(a) binding the analog to the solid phase binding member, the binding occurring in the test sample into which the binding member is placed, the binding member comprising:
(i) a solid support having micropores;
(ii) a ligand covalently attached to a water-soluble polymer, wherein:
(A) the polymer is reversibly water-soluble before its application to the solid support, the polymer being in its solid phase aggregated by noncovalent interactions and impregnates at least a portion of the micropores of the solid support in such a manner that the test sample can penetrate the micropores of the solid support noncovalently impregnated with the polymer; and
(B) the ligand is capable of interacting, directly or indirectly, so as to specifically bind with the analyte;
(b) removing the binding member from the test sample and washing the binding member, thereby separating analyte bound to the binding member from unbound analyte; and
(c) then determining the presence of the analyte bound to the binding member by reacting the washed binding member with a signal producing system that produces a detectable product when analyte is bound to the binding member, the detectable product also being bound to the binding member.

45. The binding member of claim 1 wherein the polymer is a non-protein polymer.

46. The binding member of claim 18 wherein the polymer is a non-protein polymer.

47. The binding member of claim 19 wherein the polymer is a non-protein polymer.

48. The binding member of claim 20 wherein the polymer is a non-protein polymer.

49. An apparatus for detecting an analyte in a test sample wherein the binding member of claim 45, 46, 47, or 48 is incorporated on an inner liquid-contacting surface of a test device in the form of a vessel.

50. The binding member of claim 33 wherein the polymer is a non-protein polymer.

51. The binding member of claim 42 wherein the polymer is a non-protein polymer.

52. The binding member of claim 43 wherein the polymer is a non-protein polymer.

53. The binding member of claim 44 wherein the polymer is a non-protein polymer.

* * * * *

UNITED STATES PATENT AND TRADEMARK OFFICE
CERTIFICATE OF CORRECTION

PATENT NO. : 5,013,669

DATED : May 7, 1991

INVENTOR(S) : Peters, Jr., et al.

It is certified that error appears in the above-identified patent and that said Letters Patent is hereby corrected as shown below:

Col. 1, line 30 reads "drugtesting"; should read --drug testing--.

Col. 4, lins 14-15 reads "IIgand Is" should read --ligand is--.

Col. 4, line 51 reads "1-ethyl-3-3dimethylaminopropyl)" should read
  -- 1-ethyl-3 (3-dimethylaminopropyl)--

Col. 4, line 53 "iigand" should read "ligand".

Col. 9, lines 23-24 "water for" should read --water. For--

Col. 9, line 26 "1-ethyl-3-3dimethylaminopropyl)" should read
  -- 1-ethyl-3 (3-dimethylaminopropyl)--

Col. 9, line 51 reads "NaCI" should read --NaCl--.

Col. 10, line 18 reads "$C(NH_2)^{30}$" should read --$C(NH_2)^{+}$--.

Col. 10 line 41 reads "is the reacted" should read --is then reacted--.

Col. 11, line 12 "For man" should read --For many--.

Col. 12, line 44 "anY" should read --any--.

Col. 13, line 7 "NaCI or KCI" should read --NaCl or KCl--.

Col. 14, line 47, "1-ethyl-3-3dimethylaminopropyl)" should read
  --1-Ethyl-3-(3-Dimethylaminopropyl)--

Col. 15, line 25 "N," should read --$N_2$--.

Col. 16, line 6 "Ravon" should read --Rayon--.

UNITED STATES PATENT AND TRADEMARK OFFICE
CERTIFICATE OF CORRECTION

PATENT NO. : 5,013,669

DATED : May 7, 1991

INVENTOR(S) : Peters, Jr., et al.

It is certified that error appears in the above-identified patent and that said Letters Patent is hereby corrected as shown below:

Col. 17, line 26, "Ravon" should read --Rayon--

Col. 17, line 41 reads "Tris-HCI pH" should read --Tris-HCl pH--.

Col. 19, line 2 reads "iigand" should read --ligand--.

Col. 23, line 48 reads "(a) binding the analog to the solid phase" should read --(a) binding the analyte to the solid phase--.

Signed and Sealed this

Twenty-fourth Day of May, 1994

Attest:

BRUCE LEHMAN

*Attesting Officer*     *Commissioner of Patents and Trademarks*